United States Patent [19]

Boudakian

[11] 4,075,252
[45] Feb. 21, 1978

[54] DIAZOTIZATION-FLUORINATION IN A MEDIUM OF HYDROGEN FLUORIDE-CONTAINING AMMONIUM IONS

[75] Inventor: Max M. Boudakian, Pittsford, N.Y.

[73] Assignee: Olin Corporation, New Haven, Conn.

[21] Appl. No.: 707,975

[22] Filed: July 23, 1976

Related U.S. Application Data

[63] Continuation-in-part of Ser. No. 627,874, Oct. 31, 1975, abandoned.

[51] Int. Cl.² .............................................. C07C 25/13

[52] U.S. Cl. .......................... 260/649 F; 260/290 HL
[58] Field of Search ..................... 260/290 HL, 649 F

[56] References Cited

U.S. PATENT DOCUMENTS 3,798,228   3/1974   Boudakian et al. ........... 260/290 HL Primary Examiner—Alan L. Rotman
Attorney, Agent, or Firm—William A. Simons; Thomas P. O'Day; F. A. Iskander

[57] ABSTRACT

Process for diazotization-fluorination of aromatic or heterocyclic amines in a solution of hydrogen fluoride containing ammonium ions.

11 Claims, No Drawings

DIAZOTIZATION-FLUORINATION IN A MEDIUM OF HYDROGEN FLUORIDE-CONTAINING AMMONIUM IONS

CROSS-REFERENCES TO RELATED APPLICATIONS

This application is a continuation-in-part application of U.S. patent application Ser. No. 627,874, filed Oct. 31, 1975, now abandoned.

BACKGROUND OF THE INVENTION

1. Field of Invention

The present invention relates to an improved process for preparing fluoroaromatics or fluoropyridines by diazotization-fluorination of selected aromatic or heterocyclic amines in hydrogen fluoride. More particularly, the invention relates to processes in which a suitable amine substrate is diazotized with a diazotization agent in hydrogen fluoride to form a corresponding diazonium fluoride and the diazonium fluoride is decomposed to form a corresponding aromatic or heterocyclic fluoride. Specifically, the invention relates to the use of a solution of hydrogen fluoride containing ammonium ions as a medium in which to conduct the reaction.

2. Prior Art

Osswald et al, German Pat. No. 600,706 disclosed the conventional two-step process for diazotization-fluorination of primary aromatic amines utilizing sodium nitrite and anhydrous hydrogen fluoride. A solution was made of the amine substrate in hydrogen fluoride and sodium nitrite was added, the temperature during addition being held below about 10° C until diazotization is complete. After completion of diazotization, the reaction mixture is refluxed (temperature 30° C–40° C) to decompose the diazonium fluoride, yielding nitrogen and the corresponding aromatic fluoride. Ferm and Vander Werf, J. Am Chem. Soc., 72 4809 (1950) expanded this technology to include other substrates. Shenk et al, U.S. Pat. No. 2,563,796, modified the process by utilizing gaseous nitrosyl chloride rather than sodium nitrite in order to obtain higher decomposition temperatures.

The Osswald et al and Ferm and Vander Werf teachings have been applied to numerous aromatic and heterocyclic amine substrates and their work-up procedures have been modified over the years to improve yields and facilitate product recovery.

Nevertheless, there is still a need for further improvements and efforts have been made to modify reaction conditions to obtain increased yields and/or further simplify the overall process. One such example is found in Misaki et al., Japanese patent publication No. 81330/74, published Aug. 6, 1974 pursuant Japanese application No. 126570/72, filed Dec. 15, 1972. In accordance with this teaching, improved yields were allegedly attained in a single step diazotization-decomposition by dissolving a diazotization agent, sodium nitrite, in excess anhydrous hydrogen fluoride (generating nitrous acid in HF), separately dissolving the diazotizable amine in hydrogen fluoride, then adding the sodium nitrite in HF to the amine in HF at temperatures in the range of 30° C–50° C to simultaneously form and decompose the diazonium fluoride to the aromatic fluoride.

It has now been found that whether one employs the conventional two-step process or its modifications or the one-step process the presence of ammonium ions in the hydrogen fluoride solution or medium, surprisingly and unexpectedly, enhances yields beyond those obtainable when diazotization is conducted in HF alone, and moreover, permits the successful diazotization-fluorination in HF of substrates which with HF alone give principally tars.

SUMMARY OF THE INVENTION

The invention thus comprises an improved process for diazotization-fluorination of aromatic and unsaturated heterocyclic amines in HF wherein diazotization and decomposition is conducted in the presence of ammonium ions in the solution of hydrogen fluoride.

Additional advantages of the present process are found in the ability to recover this HF solution in accordance with the process set forth in Churchill, U.S. Pat. No. 2,939,766, instead of having to dispose of it, and in the excellent phasing of organic and inorganic layers to facilitate product work-up.

The fluorinated aromatics or pyridines produced by the present invention can be employed as chemical intermediates having a variety of applications. For example, fluorobenzene is used as an intermediate in making tranquilizers and 2-fluoropyridine is used as an intermediate in making contraceptives and other uses include insecticides and the like.

DETAILED DESCRIPTION OF THE INVENTION

The generalized reaction for the present invention may be represented by the formula

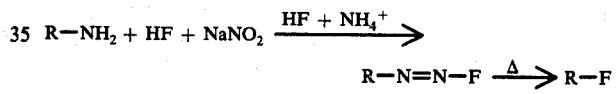

$$R-NH_2 + HF + NaNO_2 \xrightarrow{HF + NH_4^+} R-N=N-F \xrightarrow{\Delta} R-F$$

where an aminobenzene or aminopyridine substrate (R—NH$_2$) in HF is reacted with diazotization agent, represented here as sodium nitrite, to produce the corresponding diazonium fluoride, which is decomposed, usually by heat, to make the desired fluorobenzene or fluoropyridine. The improvement of the present invention over that of the prior art being the introduction of NH$_4^+$ ions in the solution of HF. Of course, the reaction may be conducted according to either the one or two step methods described above.

For the present invention, suitable substrates include aromatic primary amines and unsaturated heterocyclic primary amines having the formula (I) or (II), respectively

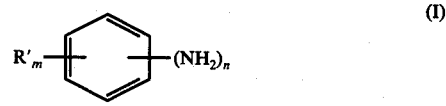

(I)

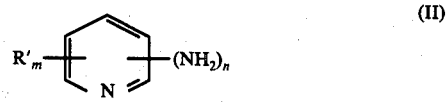

(II)

wherein R' is a ring substituent selected from the group consisting of halogen, preferably chlorine, fluorine and bromine; alkyl, preferably lower alkyl having 1–4 carbon atoms; nitro; carboxyl; hydroxy; alkoxy, preferably lower alkoxy having 1–4 carbon atoms and/or a combination thereof, $m$ is an integer having a value of 0–3 and $n$ is an integer having a value of 1–2.

Suitable aromatic substrates include, for example, o, m or p-toluidine, aniline, o, m or p-haloaniline, o, m or p-alkoxyaniline, o, m or p-aminophenols, o, m or p-nitroaniline and o, m or p-phenylene diamine. Likewise, illustrative compounds of the pyridine series include 2, 3 or 4-aminopyridine, diaminopyridines such as 2,6-diaminopyridine, haloaminopyridines such as 2-amino-4, 5 or 6-halopyridine and 3-amino-5 or 6-halopyridine, nitroaminopyridines such as 2-amino-5-nitropyridine and alkylaminopyridines such as 2-amino-4, 5 or 6-methylpyridine and 2-amino-4,6-dimethylpyridine.

The usual diazotization agents, namely, sodium nitrite, potassium nitrite, nitrous anhydride, nitrous acid and nitrosyl halides or nitrosyl halide complexes with HF may be employed in the reaction and the nitrous acid may be prepared in-situ by known methods, for example, by dissolving an alkali metal nitrite in excess hydrogen fluoride. Where diazotization-fluorination of a single amino group is to be conducted, i.e., where $n$ in formulae (I) or (II) has a value of 1, from about 1.0 to 1.5 moles of the diazotizing agent, preferably about 1.0 to 1.25, are employed per mole of substrate. Where tetrazotization, i.e., diazotization-fluorination of both amine groups of a diamine, is desired, i.e., $n$ is 2, these amounts must be doubled to about 2.0 to 3.0 moles, preferably from about 2.0 to 2.5 moles of diazotizing agent per mole of substrate.

Hydrogen fluoride acts as the source of fluorine for the reaction. Suitably, from about 2 moles up to about 30 moles of HF, preferably about 7.5 moles up to about 25 moles of HF, are employed per mole of substrate. Anhydrous HF is preferred but 70% aqueous up to anhydrous may be employed if desired. The HF should be present in excess molar quantities over that necessary for the diazotization reaction because having too little of HF present will cause the reaction to run out of control and endanger the safety of the operation. On the other hand, having too much HF present lowers the economic value of the process. Anhydrous HF is favored because aqueous HF can cause corrosion to the equipment if not carefully controlled.

In accordance with the present invention, a solution of hydrogen fluoride containing ammonium ions is utilized as the medium for both steps. As used herein, the term "ammonium ions" is used in a general sense to indicate those ions formed by adding ammonium ion-generating compounds to the solution of hydrogen fluoride. Such compounds can be either ammonium salts such as ammonium fluoride and ammonium bifluoride, ammonium fluoride solvates like $NH_4F \cdot HF$, $NH_4 \cdot 3HF$, and $NH_4F \cdot 5HF$, aqueous or anhydrous ammonia or combinations thereof. Further sources of "ammonium ions" can be other soluble non-fluoride ammonium salts as described in detail below. The preferred source of ammonium ions is ammonium bifluoride because of its relatively low cost and ease of handling.

The structure of the compound or compounds formed when a source of ammonium ions is added to the HF medium has not been ascertained. It is believed that possibly an ammonium fluoride-HF complex is formed which is at least in part, one or more of the above solvates of ammonium fluoride and HF. The generalized formula for these solvates is $NH_4F \cdot xHF$, with $x$ having one or more values in the range of about 1 to 10. It is known, for example, that when ammonium fluoride is added to HF, one or more stable solvates are formed, namely, $NH_4F \cdot 3HF$ having a melting point of $-23°$ C and/or $NH_4F \cdot 5HF$ having a melting point of $-8°$ C. Also, it is known that when aqueous or anhydrous ammonia is added to HF, there is an instantaneous reaction to form ammonium fluoride. And quite possibly, these solvates are also produced. Likewise, when other ammonium salts like ammonium bifluoride and the like are used, it is also possible that the higher solvates are made. However, this is merely a theory and the present invention is not limited thereto. The important criterion is that some source of ammonium ions be added to the solution of HF in carrying out the present process.

The amount of ammonium ion is most conveniently expressed as a molar percent of the solution of hydrogen fluoride and this molar percent can range from about 0.5 to about 35 percent of the HF solution, preferably from about 2.5 to about 15 molar percent of the HF solution. In figuring this molar percent, only the moles of ammonium ions and those of HF are used; others such as anions of ammonium salts and the like are not used. For purposes of determining these percentages, where ammonium bifluoride is utilized for example, the bifluoride is regarded as contributing one mole of HF and one mole of ammonium ion per mole of the bifluoride.

As stated before, the ammonium ions can be alternatively formed by addition of non-fluoride ammonium salts instead of the addition of the above ammonium compounds to the HF. This is accomplished by adding any suitable soluble non-fluoride ammonium salt or salts to the HF so that the ammonium cation will react with hydrogen fluoride and may form said solvates. These salts should be soluble in the reaction medium so that the ammonium cation remains in solution. The following commercial ammonium salts are illustrative of those which may be employed:

Ammonium Acetate
Ammonium Bicarbonate
Ammonium Biborate or Pentaborate
Ammonium Bichromate
Ammonium Bromide
Ammonium Chloride
Ammonium Citrate
Ammonium Fluoborate
Ammonium Molybdate or Dimolybdate
Ammonium Gluconate
Ammonium Lauryl Sulfate
Ammonium Nitrate
Ammonium Oxalate
Ammonium Persulfate
Ammonium Phosphate
Ammonium Silicofluoride
Ammonium Sulfamate
Ammonium Sulfate
Ammonium Thiosulfate
Ammonium Thiocyanate A basis and understanding of this embodiment of the invention wherein a non-fluoride ammonium salt in HF is used can be found in the treatise "Inorganic Chemistry in Liquid HF" by M.F.A. Dove and A.F. Clifford, Pergamon Press, New York, 1971, which states an page 156 that the halides of alkali metals, ammonium and substituted ammonium cations will be solvolyzed very readily to give solution of their fluorides. On the basis of this teaching, soluble non-fluoride ammonium salts can be used to generate ammonium ions in the present invention provided they do not cause any appreciable hindrance or interference to the diazotizing or decomposing steps or will not be susceptible to diazotization itself. And thus, it is to be understood that the ammonium compounds added to the HF solution can be in the form of either the above-noted ammonium fluoride compounds, ammonia (aqueous or anhydrous), or soluble non-fluoride ammonium salts.

The diazotization-fluorination process may be conducted in at least two basic ways; as a single step diazotization-decomposition or as a two-step process in which diazotization is effected at low temperature and then the reaction mixture is heated to effect decomposition.

In the two-step process the diazotization is conducted at a temperature in the range of $-20°$ C to about $10°$ C, preferably $-10°$ C to about $10°$ C, and this diazotization step is conducted in the usual manner by slowly adding the diazotization agent to a mixture of the substrate and the ammonium fluoride in HF. Alternatively, the first step may be started without the addition of the ammonium ion-generating compounds and then add these compounds to the reaction mixture part way through the first step. Thereafter, the reaction mixture is heated to decomposition temperature which is the temperature at which nitrogen evolution becomes substantially complete. Generally, depending on which diazonium fluoride intermediate is being decomposed, this will occur by the time the temperature reaches the reflux temperature of the reaction mixture, namely, about $40°$ C–$50°$ C. In other instances, higher temperatures are required and usually these may be attained by heating under pressure or evaporating solvent until the desired temperature is reached. It should be noted that "decomposition" is defined herein as the removal of $N_2$ from the diazonium fluoride, preferably as shown by increased temperature. However, other methods, if applicable, could be used.

With some diazonium fluorides, however, notably certain o-substituted diazonium fluorides, tar formation may result if either of these techniques is employed. These may advantageously be decomposed by contacting the reaction mixture with a suitable heat exchange medium at a temperature above the distillation temperature of the resulting product as described in U.S. Pat. No. 3,950,444, for example, $100°$ C–$350°$ C.

If it is desired to conduct the reaction in a single step, the diazotization agent is dissolved in one portion of the HF, the substrate in another with HF containing the ammonium ions added to one or both. The diazotization agent in HF is then added slowly to the substrate in HF at a temperature above the decomposition temperature of the diazonium fluoride. Suitable temperatures for the one-step reaction thus fall within the range from about $15°$ C to about $50°$ C, that is from as low as the temperature at which decomposition begins to the reflux temperature of the reaction mixture. If that is not sufficiently high, then the reaction can be conducted under pressure to attain higher temperatures.

It is apparent from the foregoing discussion that depending on the technique for conducting the reaction and on the particular substrate that diazotization temperatures may vary within the range of $-20°$ C up to about $50°$ C and that decomposition temperatures may vary in the range of about $15°$ C up to about $350°$ C, preferably $15°$ C up to about $100°$ C.

It is also apparent that it is preferable to operate at atmospheric pressure but that lower or higher pressures may be used as desired for most substrates, for example, 0.5 to 50 atmospheres, advantageously 0.8 to about 1.5 atmospheres.

Where either a one or two-step process is employed, the decomposition time will vary with the speed at which the diazotization agent is added and/or with the temperature. Where a heat exchange medium is used, the decomposition is instantaneous, where a two-step process is utilized, the decomposition time will depend on the speed at which temperature is increased and, in the one-step process, on the speed at which the diazotization agent is added to the substrate/HF mixture. Decomposition time may thus vary from about 0.5 seconds up to about 25 hours.

The present process can be carried out in any conventional chemical reactor which is suitable for this purpose. The reactor can be made out of stainless steel or plastics such as chlorotrifluoroethylene or tetrafluoroethylene polymers. The preferred is a conventional type 304 stainless steel reactor.

The following examples further illustrate the invention:

EXAMPLE 1

Fluorobenzene Synthesis Two-Step Process in HF/Ammonium Bifluoride

A 1-liter ss (i.e., stainless steel) 304 reactor cooled at $-10°$ C was successively charged with anhydrous HF (14 moles; 280 g), ammonium bifluoride (1.0 mole; 57.1 g) and aniline (1.0 mole; 93.1 g). Diazotization was accomplished by the addition of sodium nitrite (70.2 g; 1.02 moles) at $0°$ C $\pm$ $5°$ C.

Phenyl diazonium fluoride was then decomposed at $18°$ C–$44°$ C during a 6 hour period. After the decomposition was complete (no gas evolution), the mixture was cooled to $0°$ C and transferred to a Teflon separatory funnel. Immediate separation of the organic and aqueous HF (light green) layers occurred.

The upper organic layer (wt. 100 g) was phased, neutralized by addition to $\sim 10\%$ NaOH and steam distilled to give a colorless liquid, wt. 76.5 g (VPC: 99.9% fluorobenzene; 0.795 mole or 79.5% yield).

Neutralization of the HF layer (wt. 367.2 g) by 29% $NH_4OH$, followed by steam distillation gave no additional organic product.

EXAMPLE 2

Fluorobenzene Synthesis Two-Step Process Utilizing in HF Alone

Example 1 is repeated utilizing no ammonium bifluoride 15 moles of HF per mole of aniline. Average yield of fluorobenzene was about 75%.

EXAMPLE 3

Fluorobenzene Synthesis One-Step Process in HF/Ammonium Bifluoride

To a 1-liter ss 304 reactor cooled at $-10°$ C was charged anhydrous HF (240 g; 12 moles), followed by addition of $NaNO_2$ (75.9 g; 1.1 moles) at $0°$ C $\pm$ $5°$ C (1.75 hour period). The solution of HONO/HF was stored at $0°$ C prior to addition to the substrate.

To a 2-liter ss 304 reactor cooled at $-10°$ C was charged anhydrous HF (140 g; 7 moles), followed by successive addition of ammonium bifluoride (1.0 mole; 57.1 g) and aniline (1.0 mole; 93.1 g). This solution of aniline hydrofluoride was then heated to $35°$ C and the liquid HONO/HF added sub-surface during a 2.5 hour period. The reaction mixture was then heated at 38° C–41° C for 1.0 hour.

The then-cooled (0° C) fluorination mixture was transferred to a Teflon separatory funnel. Phasing provided an organic (wt. 108.5 g) and a lower HF (444.2 g) layer. Neutralization of the organic layer with ~10% NaOH, followed by steam distillation gave 73.9 g of organic (VPC: 99.8% fluorobenzene; 0.767 mole or 76.7% yield).

Processing of the HF layer by addition to ammonium hydroxide, followed by steam distillation gave no additional fluorobenzene.

EXAMPLE 4

Fluorobenzene Synthesis One-Step Process in HF Alone

Example 3 was repeated except without ammonium bifluoride. Yield of fluorobenzene was 52%. Phasing of the organic and inorganic layers was poor.

EXAMPLE 5 o-Fluorotoluene Synthesis Two-Step Process in HF/Ammonium Fluoride

A 1-liter ss 304 reactor cooled at −10° C was successively charged with anhydrous HF (20 moles; 400 g); ammonium fluoride (0.75 mole; 27.8 g) and o-toluidine (1.0 mole; 107.2 g). Diazotization was accomplished by the addition of sodium nitrite (75.9 g; 1.1 moles).

o-Tolyl diazonium fluoride was then decomposed at 13.5° C–38° C during a 5 hour period. After the decomposition was complete (no gas evolution), the mixture was cooled to 0° C and transferred to a Teflon separatory funnel.

The upper organic layer (wt. 119.5 g) was phased, neutralized by addition to ~10% NaOH and steam distilled to give a colorless liquid, wt. 87.0 g (VPC: 99.8% o-fluorotoluene; 0.788 mole or 78.8% yield).

Neutralization of the HF layer (wt. 472 g) by 29% NH$_4$OH, followed by steam distillation gave no additional organic product.

EXAMPLE 6 o-Fluorotoluene Synthesis Two-Step Process in HF Alone

Example 5 was repeated in HF alone utilizing several work-up procedures. Phasing of organic and inorganic layers was poor. There was appreciable tar formation and yields were consistently lower than when ammonium fluoride was used.

| Run | Yield | Work-Up |
|---|---|---|
| 1 | 64 % | |
| 2 | 64 % | Direct neutralization of combined layers. |
| 3 | 65.5% | Pressure fluorination. Direct neutralization of both layers. |
| 4 | 68 % | |
| 5 | 64 % | Dilution with water, phasing then work-up. |

EXAMPLE 7 m-Difluorobenzene Synthesis Two-Step Process in HF/Ammonium Fluoride

To a 1-liter ss 304 reactor cooled at −10° C is successively charged anhydrous HF (18.5 moles; 370 g), ammonium fluoride (56.3 g; 1.52 moles) and m-fluoroaniline (111.1 g; 1.0 mole). Diazotization was accomplished by the addition of sodium nitrite (84 g; 1.22 moles) at 0° C ± 5° C.

m-Fluorophenyl diazonium fluoride was then decomposed at 28° C–62° C during a 10 hour period. After the decomposition was complete (no gas evolution), the mixture was cooled to 0° C and transferred to a separatory funnel.

The HF layer (wt. 394 g) was phased, neutralized with ammonium hydroxide and steam distilled to give 2.7 g of organic (VPC: 10% Carbowax 20M; 52.9% m-difluorobenzene; 1.43 g; 0.013 mole). The upper organic layer (wt. 179.0 g) was neutralized by addition to 22% NaOH and steam distilled to give a colorless liquid, wt. 52.5 g (VPC: 97.6% m-difluorobenzene; 51.2 g; 0.449 mole). The combined yield of m-difluorobenzene from processing of the HF and organic layers was 46.2%.

EXAMPLE 8 m-Difluorobenzene Synthesis Two-Step Process in HF Alone

To a 1-liter ss 304 reactor cooled at −10° C is successively charged anhydrous HF (20 moles; 400 g) and m-fluoroaniline (111.1 g; 1.0 mole). Sodium nitrite (84 g; 1.22 moles) was then added at 0° C ± 5° C.

m-Fluorophenyl diazonium fluoride was then decomposed at 38° C–55° C during a 9.5 hour period.

After the decomposition was complete (no gas evolution), the reaction mixture was cooled (0° C) and neutralized by addition to a vessel containing 29% ammonium hydroxide. Steam distillation provided m-difluorobenzene in only 2.8% yield; the steam distillation liquor contained appreciable tars (268.7 g).

EXAMPLE 9 m-Fluoroanisole Two-Step Process in HF/Ammonium Bifluoride

To a 1-liter ss 304 reactor cooled at −10° C is successively charged with anhydrous HF (19 moles; 380 g), ammonium bifluoride (1.0 mole; 57.1 g) and m-anisidine (1.0 mole; 123.2 g). Diazotization was accomplished by the addition of sodium nitrite (1.2 moles; 82.8 g) at 0° C ± 5° C.

m-Methoxyphenyl diazonium fluoride was then decomposed at 13° C–56° C during a 7 hour period. After the decomposition was complete (no gas evolution), the mixture was cooled to 0° C and neutralized by addition to 29% ammonium hydroxide (to pH 9).

Steam distillation provided an organic product, wt. 44.0 g, (VPC assay: 98.3%), which corresponded to 34.3% yield of m-fluoroanisole.

EXAMPLE 10 m-Fluoroanisole Two-Step Process in HF Alone

Example 9 was repeated utilizing 20 moles of HF in three runs. In two of the runs only tars were produced. In a third run an 11% yield was obtained in addition to substantial tar formation.

EXAMPLE 11

2-Fluoropyridine Synthesis Two-Step Process in HF/Ammonium Fluoride

A 1-liter ss 304 reactor cooled to 0° C is successively charged with anhydrous HF (20 moles, 400 g), ammonium fluoride (0.75 mole; 27.8 g) and 2-aminopyridine (1.0 mole; 94.1 g). Diazotization is accomplished by the addition of sodium nitrite (75.9 g; 1.1 moles) at 0° C ± 5° C.

The reaction mixture is then heated until decomposition of pyridyl diazonium fluoride is complete. After completion (no gas evolution), the mixture is transferred to a Teflon separatory funnel.

The upper organic layer is phased, neutralized by addition to an aqueous caustic solution, steam distilled and 2-fluoropyridine recovered.

EXAMPLE 12

2,6-Difluoropyridine Synthesis Two-Step Process in HF/Ammonium Fluoride

A 1-liter ss 304 reactor cooled to 0° C is successively charged with anhydrous HF (20 moles; 400 g) ammonium fluoride (56.3 g; 1.52 moles) and 2,6-diaminopyridine (1.0 mole, 109.1 g). Diazotization is accomplished by the addition of sodium nitrite (2.4 moles, 155.6 g) at 0° C ± 5° C over a 1 hour addition time to form a reaction mixture of 2,6-pyridyl bis-diazonium fluoride.

The reaction mixture is then decomposed by heating at 40° C–70° C over a 14 hour period. After decomposition is complete (no gas evolution), the reaction mixture is cooled and neutralized in aqueous sodium hydroxide. 2,6-Difluoropyridine is recovered from the basic mixture by steam distillation.

What is claimed is:

1. In a process for preparing a fluorobenzene by (1) diazotizing a corresponding aminobenzene substrate in the presence of hydrogen fluoride and a diazotization agent selected from the group consisting of sodium nitrite, potassium nitrite, nitrous anhydride, nitrous acid, a nitrosyl halide, and a complex of a nitrosyl halide with hydrogen fluoride, to produce a corresponding diazonium fluoride and (2) decomposing said diazonium fluoride, the improvement which comprises: conducting said diazotization and decomposition steps in a solution of hydrogen fluoride containing ammonium ions.

2. The process of claim 1 wherein said ammonium ions are formed by adding to the hydrogen fluoride an ammonium ion generating compound selected from the group of anhydrous ammonia, aqueous ammonia, ammonium fluoride, ammonium bifluoride, a solvate of ammonium fluoride with hydrogen fluoride, a soluble non-fluoride ammonium salt, and combinations thereof.

3. The process of claim 2 wherein said ammonium ions are present in a concentration from about 0.5 to 35 mole percent of the hydrogen fluoride solution.

4. The process of claim 3 wherein said solution of hydrogen fluoride is present in a range from about 2 moles to about 30 moles per one mole of said aminobenzene.

5. The process of claim 4 wherein said diazotization and said decomposition steps are carried out in separate steps.

6. The process of claim 3 wherein said diazotization and said decomposition steps occur in one step.

7. The process of claim 4 wherein said diazotization and decomposition steps are conducted in a solution of hydrogen fluoride containing from about 2.5 to 15 mole percent of ammonium ion, and from about 7.5 to about 25 moles of hydrogen fluoride are present per one mole of said aminobenzene.

8. The process of claim 7 wherein said ammonium ions are formed by adding ammonium bifluoride to said hydrogen fluoride.

9. The process of claim 8 wherein the aminobenzene is selected from the group of aniline, toluidine, fluoroaniline and anisidine.

10. The process of claim 9 wherein o-fluorotoluene is produced by diazotizing o-toluidine with sodium nitrite and anhydrous hydrogen fluoride.

11. The process of claim 10 wherein said diazotization and decomposition steps occur in separate steps.

* * * * *